US00PP14752P2

(12) United States Plant Patent
Weaver

(10) Patent No.: US PP14,752 P2
(45) Date of Patent: May 4, 2004

(54) APPLE TREE NAMED 'WEAVER'

(50) Latin Name: *Malus domestica*
Varietal Denomination: Weaver

(75) Inventor: Edgar A. Weaver, Morgantown, PA (US)

(73) Assignee: Adams County Nursery, Inc., Aspers, PA (US)

( * ) Notice: Subject to any disclaimer, the term of this patent is extended or adjusted under 35 U.S.C. 154(b) by 0 days.

(21) Appl. No.: 10/337,448

(22) Filed: Jan. 7, 2003

(51) Int. Cl.[7] ..... A01H 5/00

(52) U.S. Cl. ..... Plt./162

(58) Field of Search ..... Plt./162, 161

*Primary Examiner*—Bruce R. Campell
*Assistant Examiner*—Susan B. McCormick
(74) *Attorney, Agent, or Firm*—James A. Lucas; Driggs, Lucas, Brubaker & Hogg Co LPA

(57) ABSTRACT

A new and distinct strain of apple, designated Weaver cultivar, originated as a limb sport on a 'Fulford Gala' tree. The fruit are 1.5 to 2.5 cm larger than parent tree fruit, which will greatly improve fresh fruit packout over the existing 'Gala' strains. The tree is easier to manage than other 'Gala' strains, as tree height, trunk diameter and terminal shoot length are reduced.

2 Drawing Sheets

Latin name of genus and species: *Malus domestica.*
Variety name: Weaver.

BACKGROUND OF THE DISCLOSURE

This invention relates to apple trees and, more specifically, to an apple tree referred to as a strain, or bud mutation, of *Malus domestica* Borkh. 'Fulford Gala' (U.S. Plant Pat. No. 7,589).

I discovered this new and unique strain of apple tree as a limb sport on 'Fulford Gala' in a cultivated area near Morgantown, Pa. The tree of this invention produces a fruit of attractive commercial value, with significantly larger size than the parent (U.S. Plant Pat. No. 7,589), the original 'Gala' (U.S. Plant Pat. No. 3,637), or other 'Gala' strains (U.S. Plant Pat. No. 4,121, 6,172, 6,955, 7,396, 8,621, 8,673, 8,720, 9,681, 10,016, 10,114, 10,458, 10,840, 12,842) (all of which produce small to medium-size fruit). Tree size is more compact than 'Fulford' and other 'Gala' strains (which tend to be overly vigorous).

This new strain of apple tree was asexually reproduced by grafting near Aspers, Pa., and such reproduction has shown this new strain to come true in two successive generations. This propagation of the new strain by grafting under standard controlled conditions clearly discloses the continued maintenance of the characteristics described herein which distinguish this new strain from the parent cultivar.

SUMMARY OF THE INVENTION

This new and distinctive strain of apple tree produces a fruit 1.5 to 2.5 cm larger in diameter than 'Fulford Gala.' Tree height and trunk diameter are 50 to 70% less than 'Fulford Gala.'

DESCRIPTION OF THE DRAWINGS

This new strain of apple tree is illustrated by the accompanying photographic drawings, depicting the plant by the best possible color representation using color photography.

BOTANICAL DESCRIPTION OF THE PLANT

Figure 1:
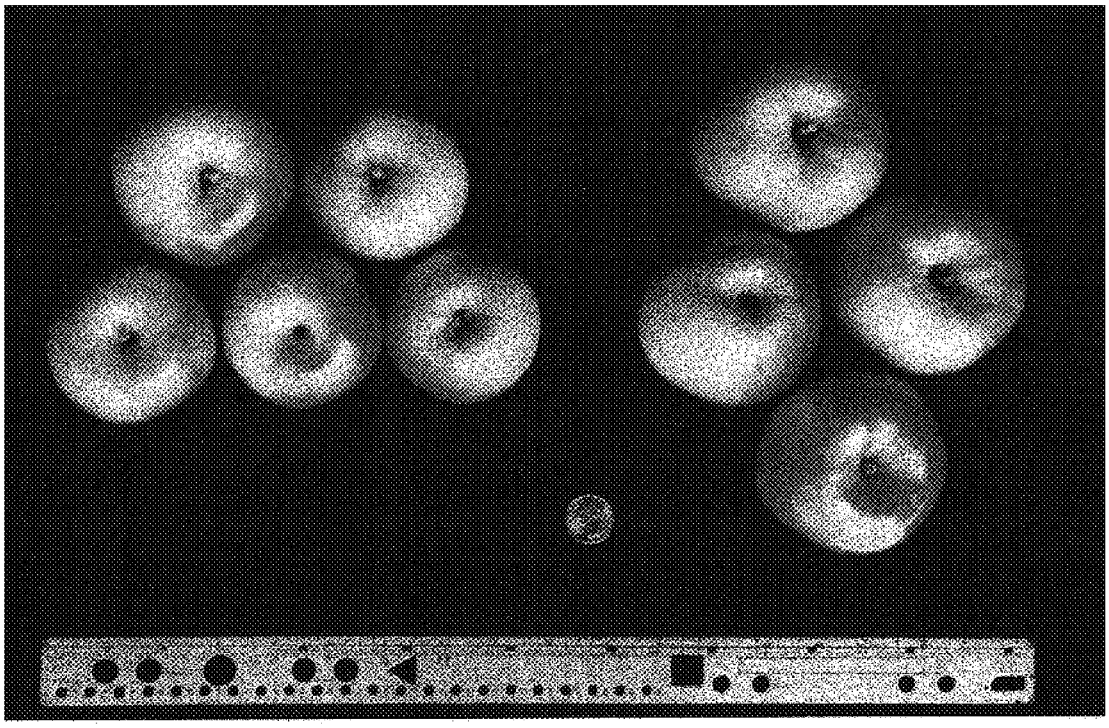
FIG. 1: At right, 4 specimens of fruit from the new tree, compared to at left, 5 specimens of fruit from the parent tree, demonstrating relative size. Fruit calyx and stem end characteristics also are shown.
Figure 2:
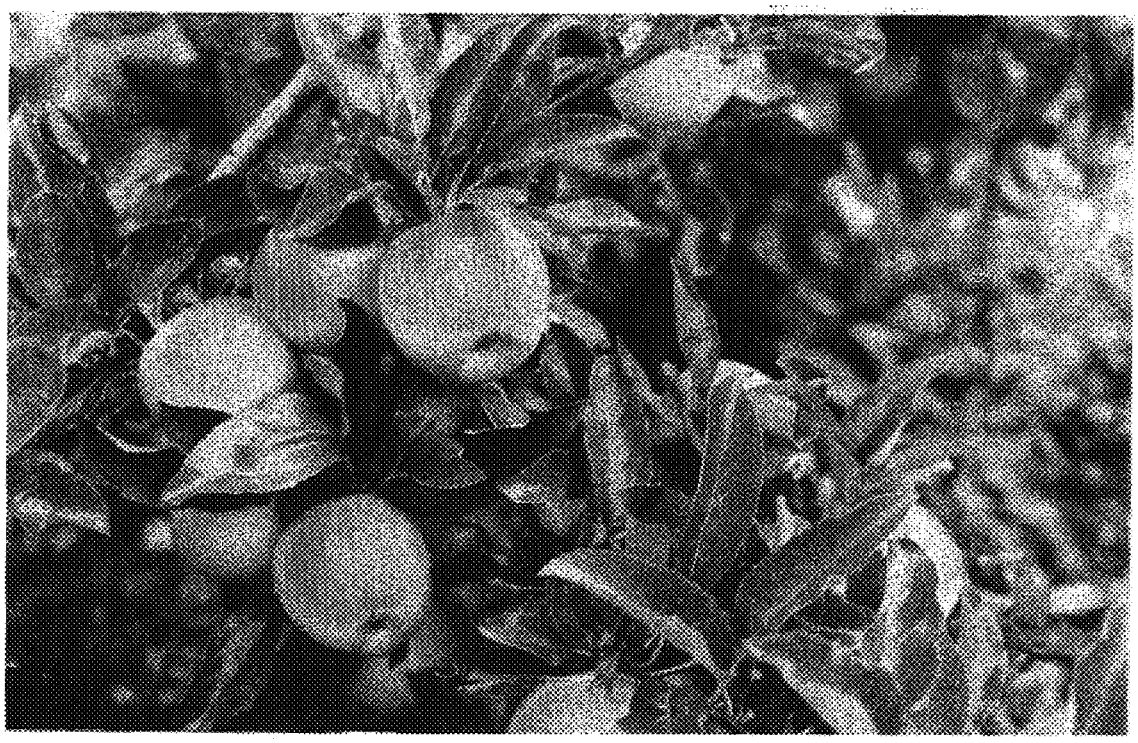
FIG. 2: Close-up of representative specimens of fruit on the new tree in different orientations to reflect characteristic size, shape, color and finish. Photo also shows semi-spur-type tree growth pattern (e.g., abundance of spurs and minimal number of vegetative shoots).

All color references below are measured against The Royal Horticultural Society Colour Chart. Colors are approximate as color depends on horticultural practices, such as light level and fertilization rate, among others.

Parentage: Limb sport on a 'Fulford Gala' tree. Asexually reproduced by bud grafting.

Tree: 1.8 m tall by 1.3 m wide and 10 lbs fruit per tree, on Bud.9 rootstock, at 4 years age, near Morgantown, Pa. (compared to 2.5 m tall by 1.8 m wide 'Fulford Gala' — same rootstock and age — in an adjacent block). Upright-spreading tree of low-medium vigor, hardy, productive, annual bearer.

*Trunk.*—Diameter 2.5 cm (compared to 4.5 cm with 'Fulford Gala') at 20 cm height above soil level, moderately rough, gray, RHS (Royal Horticultural Society) 201B.

Branches: Thickness — 10 to 12 mm, minimal branching, 65 degree crotch angles, orange-brown, RHS 177A.

*Lenticels.*—Approximately 12 per $cm^2$, slightly raised compared to 'Fulford Gala,' 0.1 cm long.

*Terminal shoots.*—Average length 35 cm (compared to 40 cm with 'Fulford Gala').

Leaves:

*Length.*—8 cm (compared to 10 cm with 'Fulford Gala').

*Width.*—5.5 cm (same as 'Fulford Gala'). Semi-glossy, upward folding, less undulating than 'Fulford Gala,' ovate with acuminate apex and rounded base, medium thick, dark green, RHS 137B for upper foliage surface, RHS 137C for lower surface.

*Venation.*—Reticulate pattern, green, RHS 138B.

*Margins.*—Serrulate-crenate.

*Petioles.*—Length 2 cm, diameter 2 mm at mid-section, green, RHS 138B, some red at base.

*Stipules.*—2, length 1.2 cm, green, RHS 137B.

Flowers:

*Dates of first and full blossoms.*—April 18 and 20, in Morgantown, Pa. in 2002 (a year when full bloom on apple trees averaged one week ahead of schedule). Early-midseason bloom period.

*Size — flower diameter.*—5.5 cm.

*Flower petals.*—5, length 24 mm, width 12 mm, shape ovate, texture soft, color white (RHS 155D) with pink (RHS 39D) venation (Venation more pronounced on abaxial surface).

Flower bud: Length 9 mm, diameter 7 mm, ovoid, white (RHS 155D) with pink (RHS 39D) venation and blush.

*Sepals.*—Length 7 mm, green (RHS 137C).

Fruit:

*Maturity when described.*—Ripe.

*Date.*—Aug. 22, 2002.

*Uniformity of maturity.*—Requires multiple harvests, as with other 'Gala' strains.

*Size.*—Uniformly large.

*Diameter.*—8.25 cm (compared to 6.50 cm with 'Fulford Gala').

*Form.*—Round to conic, regular cross-section.

*Cavity.*—Rounded, depth 16 mm, breadth 20 mm, gold-russet markings.

*Stem.*—Light green, RHS 139D, some brown, RHS 177A, lightly pubescent, length 18 mm, diameter 3 mm, 1 to 2 bracts.

*Basin.*—Depth 6 mm, breadth 23 mm.

*Calyx.*—Half-open, sepals erect, diameter 7 mm.

*Skin.*—Medium thick, glossy with medium cuticle wax.

*Lenticels.*—Medium size, moderate number, circular, yellow-white, RHS 158B, scattered over most of surface.

*Russet.*—Slight, mainly around cavity, gold, RHS 163B.

*Ground color.*—Yellow RHS 10B.

*Color markings.*—Solid blush over 50 to 80% of surface, bright red, RHS 42A.

*Bloom.*—Scant.

*Scarfskin.*—Mainly around cavity, gold, RHS 163B.

*Ground color.*—Yellow, RHS 10B.

*Color markings.*—Solid blush over 50 to 80% of surface, bright red, RHS 42A.

*Bloom.*—Scant.

*Scarfskin.*—Wanting.

*General color effect.*—Brilliant red over attractive yellow background.

*Flesh.*—Juicy, cream color, RHS 159B.

*Texture.*—Firm, fine grained, crisp.

*Flavor.*—Delicious tart/sweet blend.

*Aroma.*—Sweet, aromatic.

*Eating quality.*—Excellent, 12 to 14% soluble solids, 16 to 18 lbs. firmness at harvest maturity.

Reproductive organs:

*Pistils.*—5.

*Stamens.*—Numerous.

*Anthers.*—Yellow (RHS 11A).

*Ovary.*—Inferior.

Core: Median (equidistant between calyx and stem ends).

*Carpellary area.*—Visible.

*Depth of calyx tube.*—3 mm.

*Seed cells.*—Mostly open, 5 to 6 in number.

*Cell walls.*—Thin, reniform in longitudinal section, narrow to medium in cross-section (length 8 mm, breadth 5 mm), surface non-tufted.

Seeds: Number variable, sometimes more than 10, length 7 mm, breadth 4 mm, form acute.

*Color.*—Brown, RHS 177A.

Uses: Excellent for fresh wholesale and retail markets.

Keeping quality: Similar to 'Fulford Gala' in adjacent planting.

Resistance to insects: Similar to 'Fulford Gala' in adjacent planting.

Resistance to diseases: Significantly less fireblight than in 'Fulford Gala' in adjacent planting, possibly due to reduced terminal vigor.

Other observations: Winter hardy, moderate tolerance to drought and heat, moderate susceptibility to sunburn and stem-end cracking (similar to parent).

I claim:

1. A new and distinct strain of apple tree, as illustrated and described, characterized by improved fruit size and compact tree growth.

* * * * *